(12) United States Patent
Curci

(10) Patent No.: US 7,743,432 B2
(45) Date of Patent: Jun. 29, 2010

(54) GOGGLE WITH INTERCHANGEABLE VENT ACCESSORIES

(75) Inventor: Raymond Curci, Smithfield, RI (US)

(73) Assignee: Sperian Eye & Face Protection, Inc., Smithfield, RI (US)

( * ) Notice: Subject to any disclaimer, the term of this patent is extended or adjusted under 35 U.S.C. 154(b) by 1 day.

(21) Appl. No.: 11/461,465

(22) Filed: Aug. 1, 2006

(65) Prior Publication Data

US 2007/0113325 A1    May 24, 2007

Related U.S. Application Data

(60) Provisional application No. 60/737,922, filed on Nov. 18, 2005.

(51) Int. Cl.
*A61F 9/02*    (2006.01)
(52) U.S. Cl. ............................................. 2/435
(58) Field of Classification Search ............ 2/427, 2/428, 431, 435–439
See application file for complete search history.

(56) References Cited

U.S. PATENT DOCUMENTS

| 2,636,171 | A |   | 4/1953  | Aspenleiter |       |
|-----------|---|---|---------|-------------|-------|
| 2,654,090 | A | * | 10/1953 | Christensen et al. | 2/436 |
| 2,877,463 | A | * | 3/1959  | Watkins     | 2/437 |
| 3,141,172 | A |   | 7/1964  | Hirschmann  |       |
| 3,517,393 | A |   | 5/1970  | Beauchef    |       |
| 3,638,240 | A | * | 2/1972  | Militello   | 2/437 |
| 4,264,988 | A |   | 5/1981  | Specht      |       |
| 4,653,124 | A |   | 3/1987  | McNeal et al. |     |
| 4,689,838 | A | * | 9/1987  | Angermann et al. | 2/441 |
| 4,707,863 | A |   | 11/1987 | McNeal      |       |
| 4,785,481 | A | * | 11/1988 | Palmer et al. | 2/436 |
| 4,977,627 | A | * | 12/1990 | Metcalfe et al. | 2/437 |
| D328,084  | S |   | 7/1992  | Salce et al. |      |
| 5,363,512 | A |   | 11/1994 | Grabos, Jr. et al. |  |
| 5,652,965 | A |   | 8/1997  | Crooks      |       |
| 5,657,106 | A |   | 8/1997  | Herald, Jr. et al. |  |
| 6,049,917 | A | * | 4/2000  | Ryden       | 2/436 |
| 6,062,688 | A |   | 5/2000  | Vinas       |       |
| 6,076,196 | A | * | 6/2000  | Masumoto    | 2/436 |
| 6,138,285 | A |   | 10/2000 | Robrahn et al. |    |
| D456,037  | S |   | 4/2002  | Tabacchi    |       |
| 6,427,254 | B1|   | 8/2002  | Gardner     |       |
| D465,507  | S |   | 11/2002 | Wang        |       |
| D478,111  | S |   | 8/2003  | Huh         |       |
| 6,704,944 | B2|   | 3/2004  | Kawainshi   |       |
| 6,732,382 | B2|   | 5/2004  | Dondero     |       |

(Continued)

*Primary Examiner*—Katherine Moran
(74) *Attorney, Agent, or Firm*—Barlow, Josephs & Holmes, Ltd.

(57) ABSTRACT

Disclosed is a pair of protective eyewear that includes a frame having a brow portion with a top surface and a bottom portion with a bottom surface. The frame is configured and arranged to be secured against a wearer's face wherein the brow portion conforms to the wearer's forehead and the bottom portion conforms around the wearer's nose and cheekbones. A lens is interfittingly engaged with the frame. The frame and the lens define an interior portion of the eyewear and an exterior portion of the eyewear. The frame includes a number of vent structures, and each of the vent structures has a vent opening. The vent opening is in fluid connection between the interior portion and the exterior portion of the eyewear. The protective eyewear includes at least one vent accessory configured and arranged to releasably couple to at least one of the vent structures.

8 Claims, 7 Drawing Sheets

U.S. PATENT DOCUMENTS

| | | |
|---|---|---|
| D507,010 S | 7/2005 | Hartman |
| 6,994,433 B2 * | 2/2006 | Hockaday et al. ............. 351/62 |
| 2003/0033661 A1 * | 2/2003 | Huh .............................. 2/436 |
| 2004/0105070 A1 | 6/2004 | Hockaday et al. |

* cited by examiner

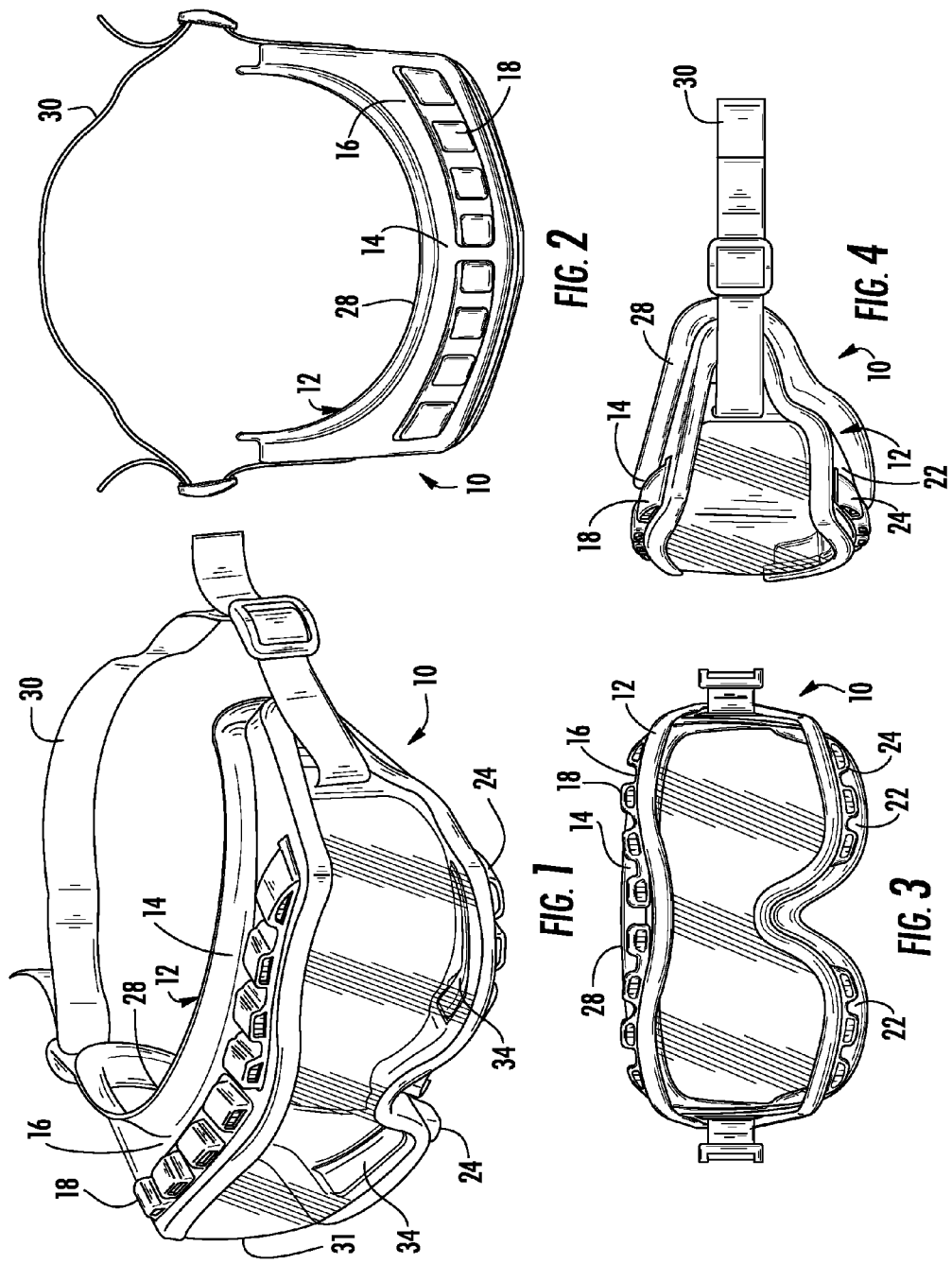

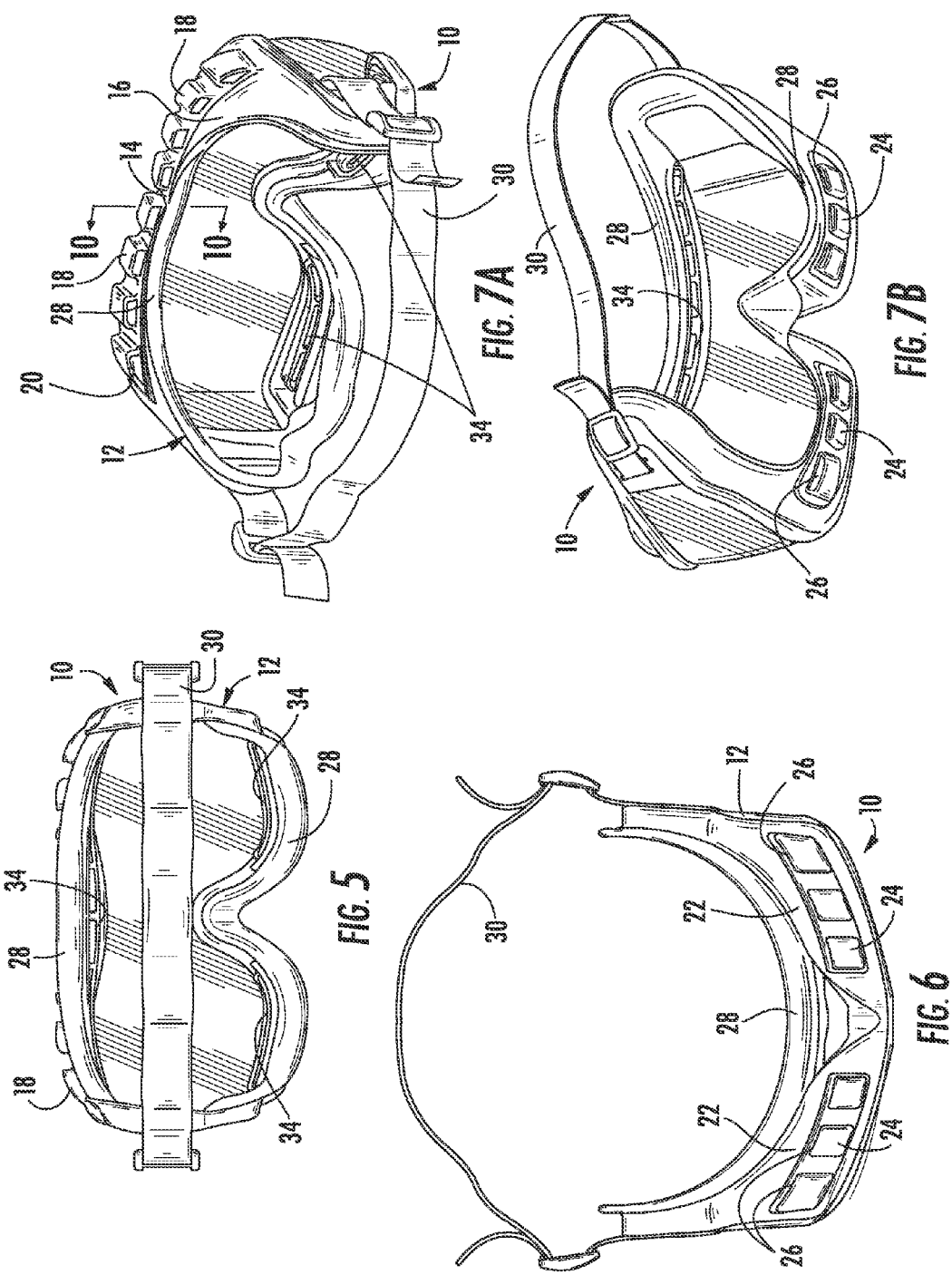

GOGGLE WITH INTERCHANGEABLE VENT ACCESSORIES

CROSS-REFERENCE TO RELATED APPLICATION

This application claims priority to earlier filed U.S. Provisional Application Ser. No. 60/737,922, filed Nov. 18, 2005, the contents of which are incorporated herein by reference.

BACKGROUND OF THE INVENTION

1. Field of the Invention

The present invention relates generally to protective or safety eyewear and more particularly to a goggle having interchangeable baffles for use with a variety of applications.

2. Background of the Related Art

Protective goggles come in a variety of configurations, but all goggles are designed to protect the wearer's eyes from foreign substances, debris, and impacts to varying degrees. Depending on the activity that the wearer is engaging in, the goggles are designed with different features. Some have a unitary lens; others have two lenses. Some have a soft rubber or plastic frame; others have a rigid frame. And yet others are designed to form a tight seal around the wearer's face to guard against splashes from dangerous or caustic liquids.

All goggles to some degree suffer from fogging of the lens or lenses due to the perspiration and warmth emanating from the wearer's face. To solve this problem, manufacturers of goggles have included vents in the goggle frame to allow moisture and heat to escape from the interior of the goggle.

However, the addition of vents is not without its drawbacks. Adding a vent necessarily means that a hole is made in the goggle frame, which can allow foreign substances, such as dust and liquids, to enter the interior of the goggle and thereby diminish the protective quality of the goggle.

To solve this problem, manufacturers of goggles have designed a variety of vent structures to prevent the incursion of foreign substances into the interior of the goggle, yet maximize airflow to prevent fogging and sweating of the lens. There are goggles designed for use in dusty environments, there are goggles designed for use when using hazardous liquids, and there are goggles that are designed for use when dealing with larger solids. Each type of goggle is designed with differently shaped vents (or no vents at all) to prevent the hazardous debris from entering the goggle, yet maintain airflow through the goggle. Some use filters; some use baffled vents; and others use covered vents. As a result, there has been an explosion in the number of goggles that are available for the end-user consumer to purchase and maintain. Therefore, there is a perceived need in the industry for a goggle that has modifiable vents for use in accordance with the underlying hazard of the activity to be engaged in.

SUMMARY OF THE INVENTION

The present invention solves the problems of the prior art by providing a safety goggle that has interchangeable vent accessories. In particular, the protective eyewear includes a frame having a brow portion with a top surface and a bottom portion with a bottom surface. The frame is configured and arranged to be secured against a wearer's face wherein the brow portion conforms to the wearer's forehead and the bottom portion conforms around the wearer's nose and cheekbones. A lens is interfittingly engaged with the frame. The frame and the lens define an interior portion of the eyewear and an exterior portion of the eyewear. The frame includes a number of vent structures, and each of the vent structures has a vent opening. The vent opening is in fluid connection between the interior portion and the exterior portion of the eyewear. A plurality of vent accessories are configured and arranged to releasably couple to the vent structures.

Because the vent accessories can be released from the frame, the end-user of the goggle merely selects the appropriate accessory according to the hazard of the activity and inserts the accessory into the vent structure. The end-user could install a baffle assembly to redirect airflow through the goggle or remove the baffle assembly entirely to allow maximal airflow. The end-user could also insert a filtered baffle assembly for use under dusty conditions, insert a plug when dealing with hazardous liquids, or insert a baffle to redirect the airflow in the goggle when dealing with hazardous materials with a reduced risk of splashing.

A unique aspect of the present invention is that the interchangeable vent accessories are located on the interior side of the goggle frame, rather than on the exterior. Locating the interchangeable vent accessories on the interior has the advantage of not interfering with the aesthetic design and look of the goggle, and further protects the vent accessories from external trauma. If the vent accessories were located on the exterior of the goggle frame, there is the distinct possibility that the vent accessories could be struck and dislodged during normal use.

Accordingly, among the objects of the present invention is the provision for a safety goggle that has interchangeable baffles.

Another object of the present invention is the provision for a safety goggle that has a reduced manufacturing cost.

BRIEF DESCRIPTION OF THE DRAWINGS

These and other features, aspects, and advantages of the present invention will become better understood with reference to the following description, appended claims, and accompanying drawings where:

FIG. 1 is a perspective view of the goggle of the present invention;

FIG. 2 is a top view thereof;

FIG. 3 is a front view thereof;

FIG. 4 is a left side view thereof, it being understood that the right side is the mirror image of the left side;

FIG. 5 is a rear view thereof;

FIG. 6 is a bottom view thereof;

FIG. 7A is a rear top perspective view thereof;

FIG. 7B is a rear bottom perspective view thereof;

DESCRIPTION OF THE PREFERRED EMBODIMENT

Figure 8:
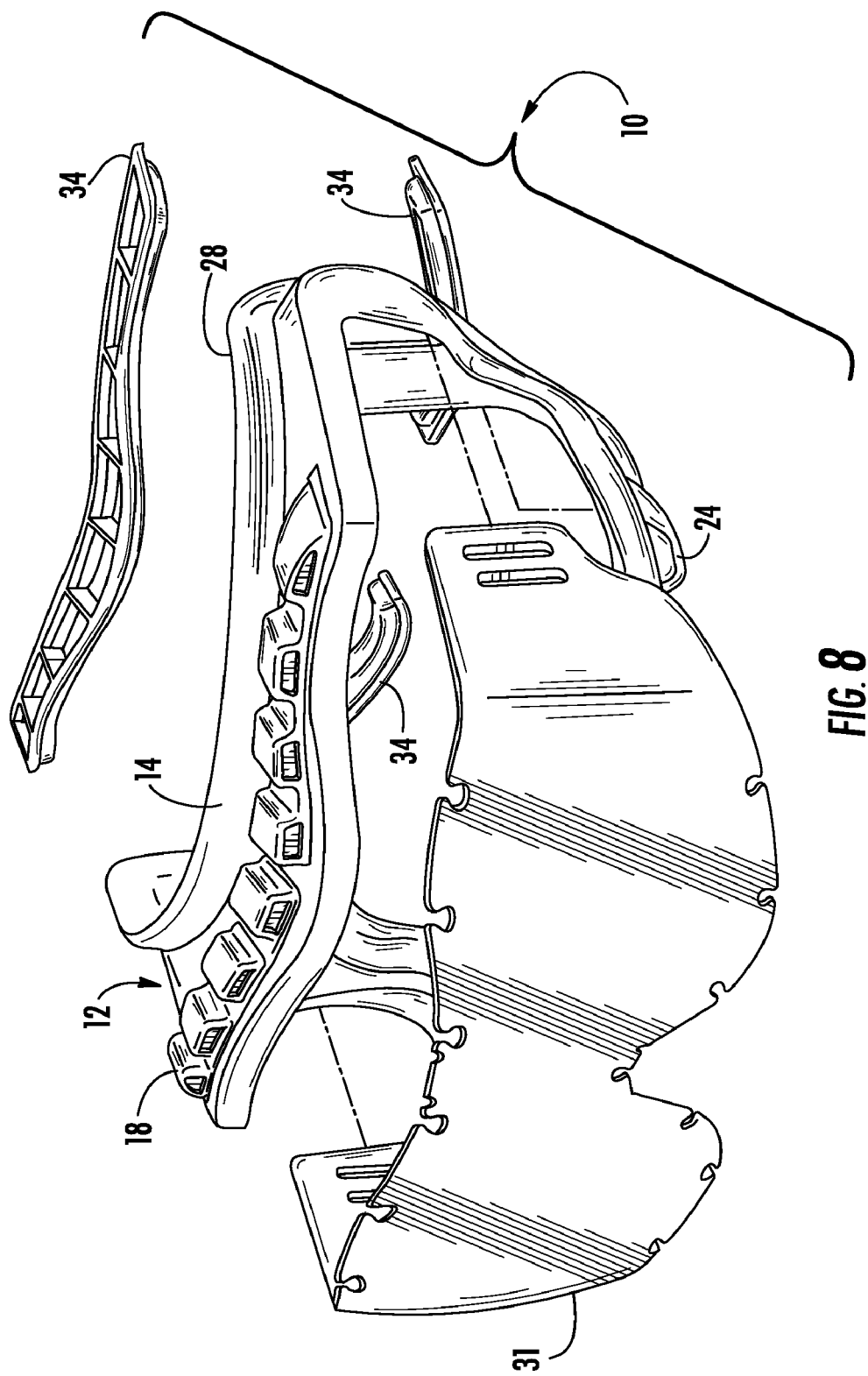
FIG. 8 is a front exploded view thereof.

Referring the FIG. 1, the goggle of the present invention is shown generally at 10.

The goggle 10 has a unitary injection molded frame 12. The frame 12 has a brow portion 14 having a top surface 16, which is best seen in FIG. 2. Projecting upwardly from the top surface 16 of the brow portion are a number of top vent structures 18 each having a rearwardly facing vent hole 20 (best seen in FIG. 7a and 7b).

The frame 12 also has a bottom portion shown in FIG. 6, which is molded to fit around the wearer's nose and over the wearer's cheek bones and has a pair of bottom surfaces 22. Projecting from these bottom surfaces are a number of left and right bottom vent structures 24 each having a rearwardly facing vent hole 26.

The top and bottom vent structures 18, 24 and the rearwardly facing vent holes 20, 26 are also prominently shown in FIGS. 7a and 7b. These vent holes 20, 26 may also be optionally molded shut.

Extending rearward and curling outward from the frame 12 is the mask seal 28, shown in FIGS. 4 and 5. The mask seal 28 rests against the wearer's face on his or her forehead, temples and cheeks just below the eye sockets and flexes to provide a comfortable fit for the wearer and establish a seal around the wearer's eyes.

Referring to FIGS. 1-7, an adjustable strap 30 is attached at either end of the frame, which the wearer can adjust to fit the goggle comfortably, yet securely to his or her head and face.

Figure 9:
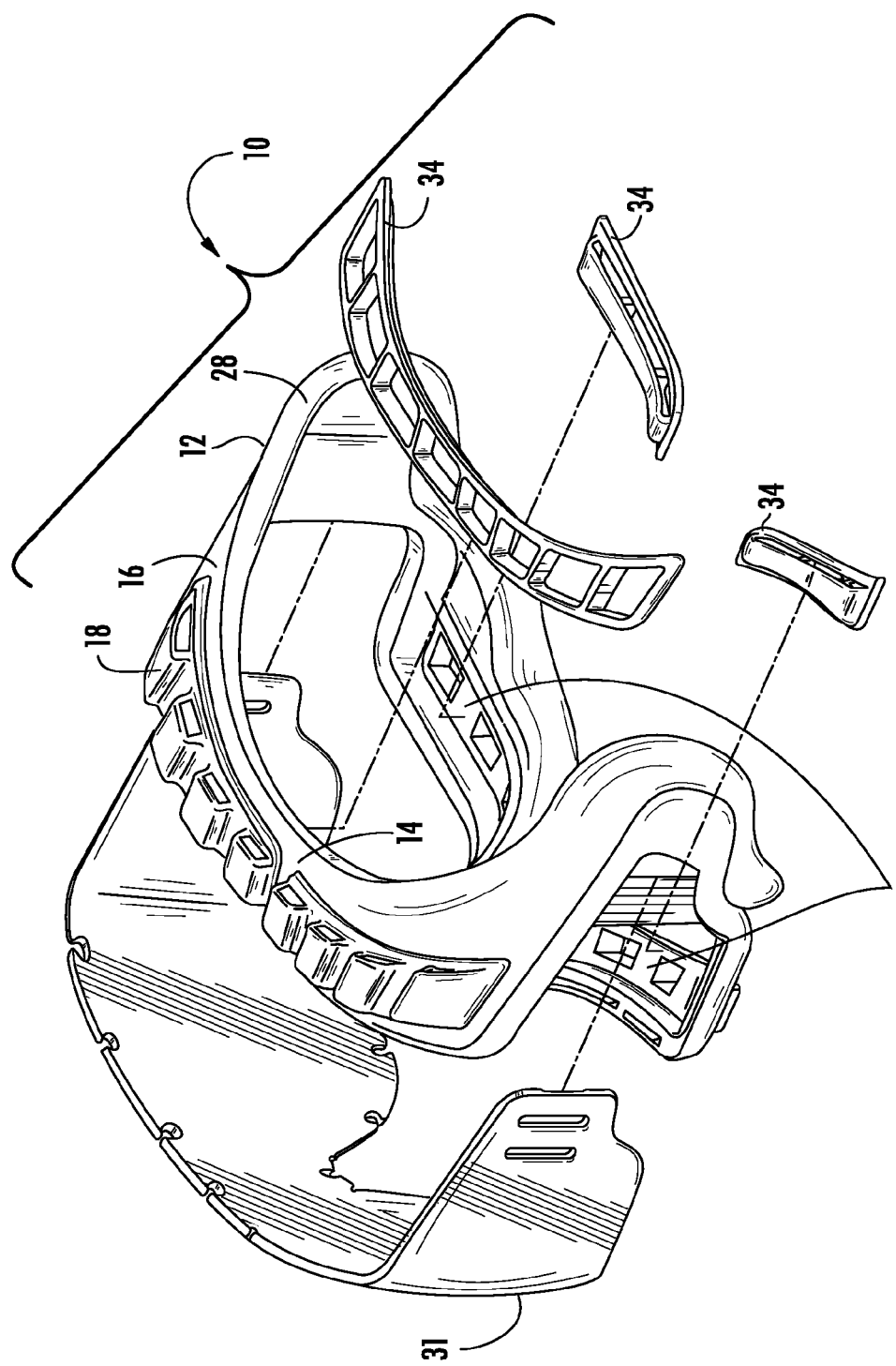
FIG. 9 is a rear exploded view thereof.

As seen in FIGS. 7-9, a unitary lens 31 is snap-received into the frame to protect the wearer's eyes.

Figure 10:
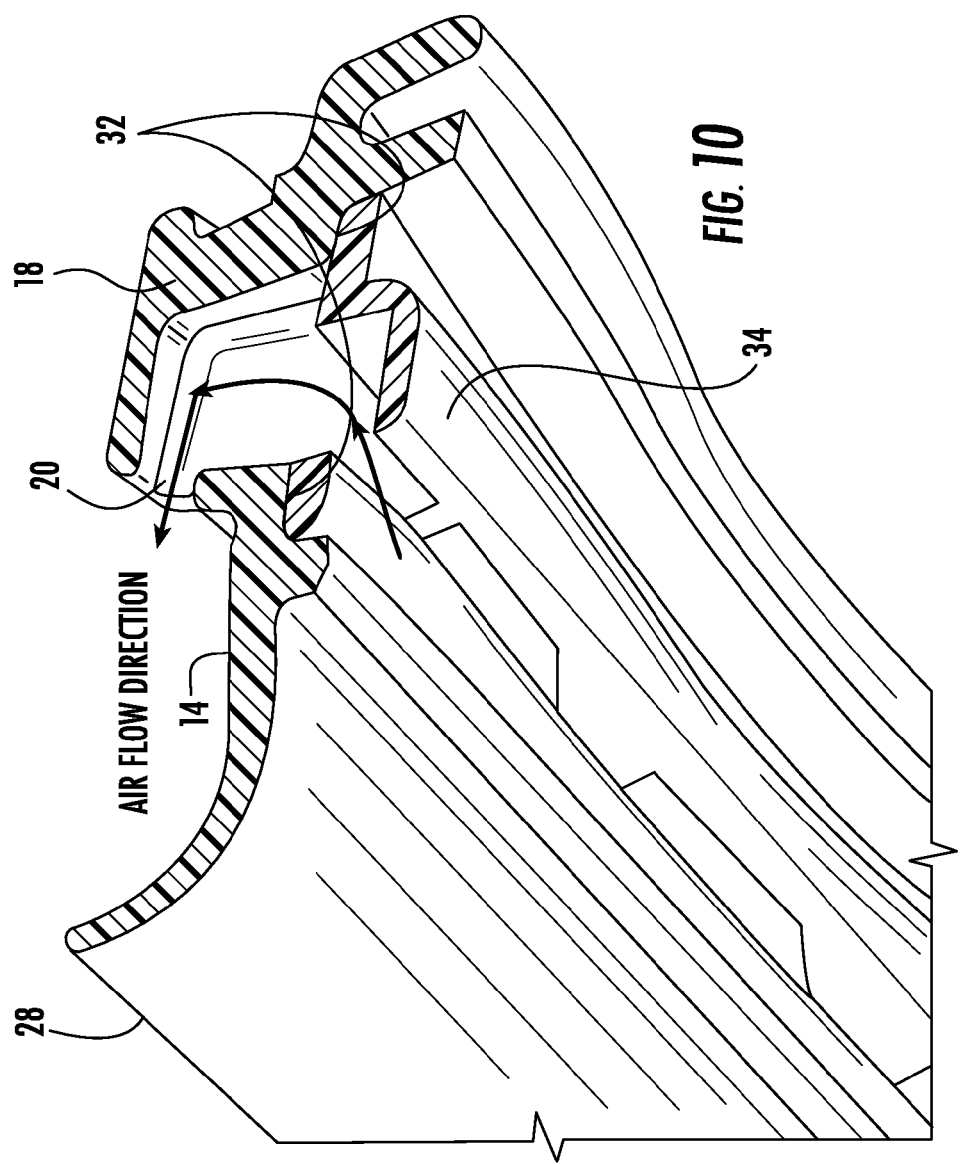
FIG. 10 is a partial cross-section view through line 10-10 of FIG. 7A (with the lens removed from the frame) showing the airflow through the baffle vent accessories and vent structures of the goggle of the present invention.

Continuing with FIGS. 7-9, the interior of the goggle frame 12 has recessed portions 32 (FIGS. 9 and 10) forming pockets opposite the top and bottom vent structures 18, 24. These recessed portions 32 are fitted with optional vent accessories 34, which may be baffles. The vent accessories 34 may be snap fit into the recessed portions 32 or even permanently glued in place. As shown in FIG. 10, the baffle vent accessories 34 redirect the airflow through the top and bottom vent structures 18, 24. Baffle vent accessories 34 provide an added measure of safety by preventing a direct route to the wearer's eyes, thus minimizing the effect of splashes of chemicals or other dangerous substances.

Figure 11B:
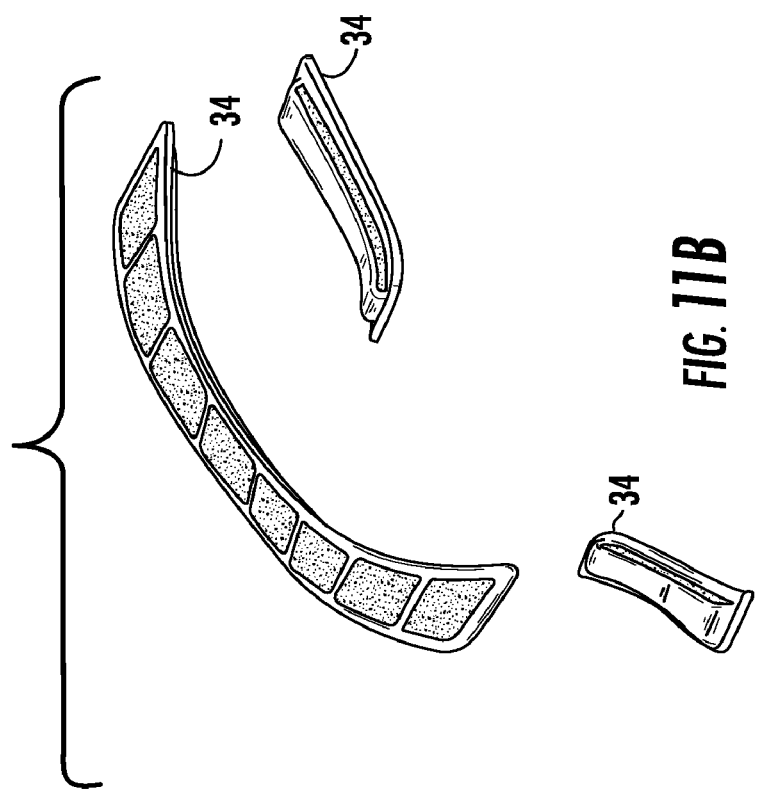
FIG. 11B is a perspective view of a filtered vent accessory with air-deflecting baffles for the goggle of the present invention.
Figure 11A:
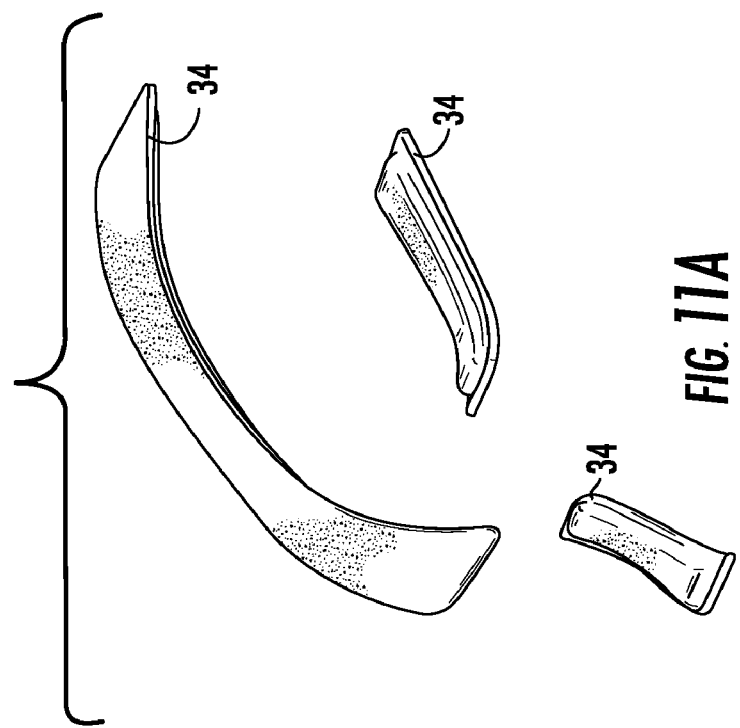
FIG. 11A is a perspective view filtered vent accessory for the goggle of the present invention.
Figure 11C:
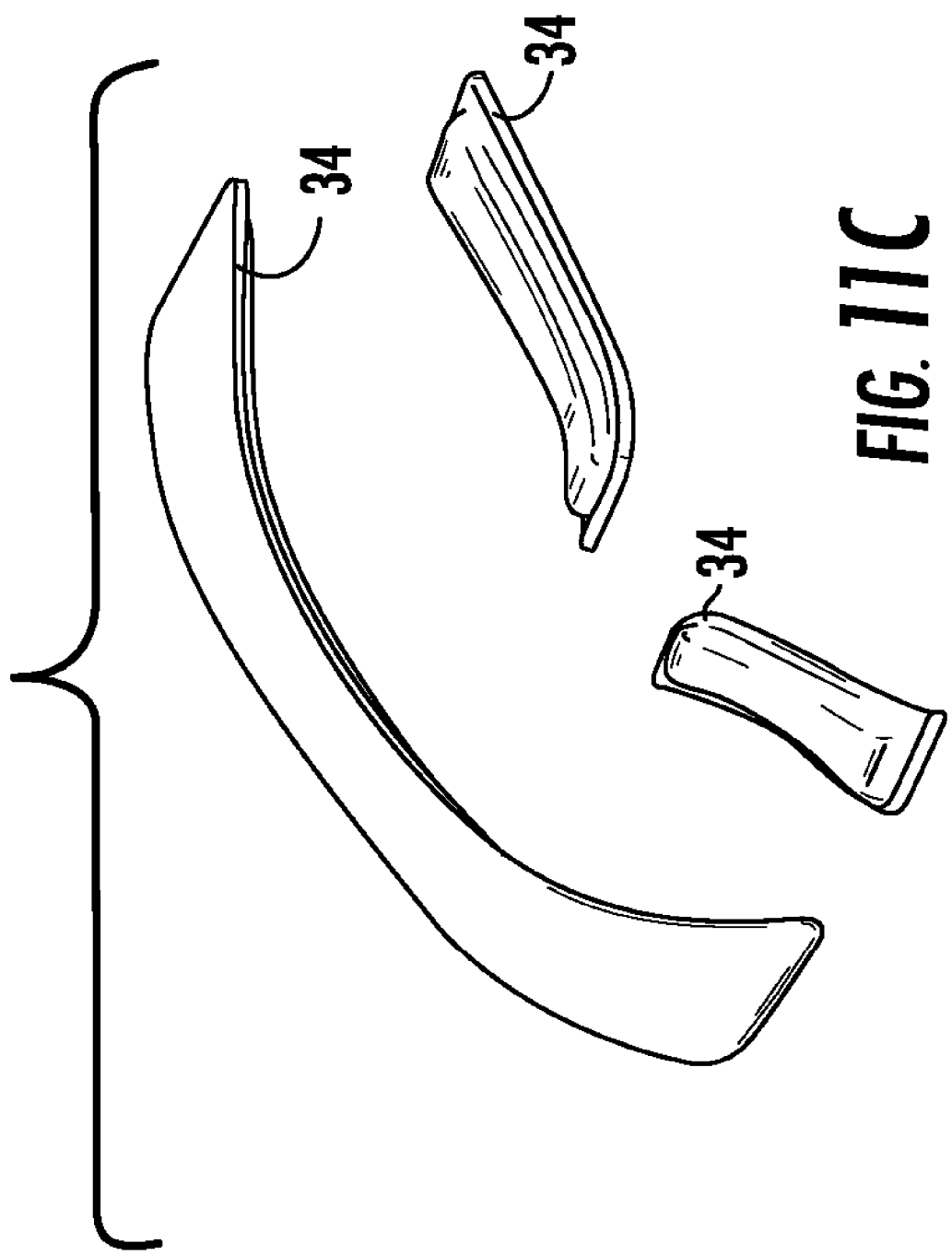
FIG. 11C is a perspective view of a plug vent accessory for the goggle of the present invention.

Alternative to baffles, the recessed portions 32 may also receive other types of vent accessories 34. For instance, filter inserts (FIG. 11a), filtered baffle inserts (FIG. 11b), or plugs (FIG. 11c) may be used as vent accessories 34. The plugs can be arranged to completely block the vent hole opening 20, 26 in each vent structure 18, 24.

Therefore, it can be seen that the present invention provides a unique solution to the solution to the problem of providing a goggle that has configurable venting structures depending on the end-use application.

It would be appreciated by those skilled in the art that various changes and modifications can be made to the illustrated embodiments without departing from the spirit of the present invention. All such modifications and changes are intended to be within the scope of the present invention except as limited by the appended claims.

What is claimed is:

1. A pair of protective eyewear, comprising:
a frame having a brow portion with a top surface and a bottom portion with a bottom surface with a plurality of vent structures extending outwardly from the top surface and bottom surface, respectively, said frame configured and arranged to be secured against a wearer's face wherein said brow portion conforms to said wearer's forehead and said bottom portion conforms around said wearer's nose and cheekbones;
a lens interfittingly engaged with said frame;
said frame and said lens defining an interior portion of said eyewear and an exterior portion of said eyewear;
said frame including at least one recessed portion forming a pocket on the interior portion, each of said plurality of vent structures having at least one rearward facing vent opening in fluid communication between said interior portion and said exterior portion of said eyewear through said recessed portion, said at least one rearward facing vent opening oriented towards said wearer's face; and
at least one vent accessory configured and arranged to releasably couple to at least one of said recessed portion of the frame, said at least one vent accessory enclosed within said interior portion of said eyewear.

2. The eyewear of claim 1, wherein said vent accessory is a baffle structure for redirecting air through said vent structure.

3. The eyewear of claim 1, wherein said vent accessory is a filter for preventing airborne particles from entering said interior of said eyewear.

4. The eyewear of claim 1, wherein said vent accessory is a plug for substantially blocking air flow through said vent structure.

5. The eyewear of claim 1, wherein said vent accessory is a filtered baffle structure for redirecting air flow through said vent structure and trapping airborne particles within said filtered baffle.

6. The eyewear of claim 1, wherein said plurality of vent structures comprises:
a top vent structure extending outwardly from said top surface of said brow portion; and
a left bottom vent structure extending outwardly from said bottom surface of said bottom portion of said frame to the left of said wearer's nose; and
a right bottom vent structure extending outwardly from said bottom surface of said bottom portion of said frame to the right of said wearer's nose.

7. The eyewear of claim 6, wherein said top vent structure further comprises a plurality of rearward facing vent openings.

8. The eyewear of claim 6, wherein said left bottom vent structure and said right bottom vent structure further comprises a plurality of rearward facing vent openings.

* * * * *